United States Patent [19]
Fahy

[11] Patent Number: 5,591,203
[45] Date of Patent: Jan. 7, 1997

[54] ANASTOMOSIS CUFF MANIPULATOR TOOL

[75] Inventor: Gregory M. Fahy, Gaithersburg, Md.

[73] Assignees: Organ, Inc.; Life Resuscitation Technologies, Inc., both of Chicago, Ill.

[21] Appl. No.: 409,519

[22] Filed: Mar. 24, 1995

[51] Int. Cl.$^6$ ..................................... A61B 17/00
[52] U.S. Cl. ........................... 606/207; 606/151; 81/420; 81/424.5; 433/159
[58] Field of Search ..................................... 606/151, 150, 606/153–157, 205–211; 623/1, 12; 81/300, 385, 405, 415, 420–424, 424.5, 426, 426.5; 433/159

[56] References Cited

U.S. PATENT DOCUMENTS

| | | | |
|---|---|---|---|
| 1,359,164 | 11/1920 | Giudice | 606/205 |
| 2,316,297 | 4/1943 | Southerland et al. | 606/205 |
| 2,507,710 | 5/1950 | Grosso | 606/205 |
| 2,977,150 | 3/1961 | Thomas | 606/207 |
| 4,635,636 | 1/1987 | Goldstein | 606/150 |
| 4,657,019 | 4/1987 | Walsh et al. | 606/153 |
| 5,188,638 | 2/1993 | Tzakis | 606/151 |
| 5,217,007 | 6/1993 | Ciaglia | 606/207 |
| 5,391,181 | 2/1995 | Johnson et al. | 606/207 |

FOREIGN PATENT DOCUMENTS 1697796  12/1991  U.S.S.R. ................. 606/210

OTHER PUBLICATIONS

Padula, Richard T., "A New Clamp for Rapid Vascular Anastomosis", Jun. 1965, Surgery Magazine vol. 57, #6 pp. 819–822.

Primary Examiner—Michael Powell Buiz
Assistant Examiner—Jeffrey A. Schmidt
Attorney, Agent, or Firm—Oliff & Berridge

[57] ABSTRACT

A manipulator tool for grasping an anastomosis cuff has two gripping fingers with indentations. When the gripping fingers are brought together, the indentations form an aperture between the gripping fingers which is used to surround and grasp the outer surface of an anastomosis cuff. The indentations can have various shapes to conform to different sizes and different shapes of cuffs. The gripping fingers may also be adjustable and replaceable. The manipulator tool may also include a latching or locking device for keeping the tool closed in a particular position.

21 Claims, 4 Drawing Sheets

ANASTOMOSIS CUFF MANIPULATOR TOOL

BACKGROUND OF THE INVENTION

The invention relates devices for performing vascular anastomosis, and more particularly to cuff manipulator tools used to grasp an anastomosis cuff during vascular anastomosis.

Many types of surgery require vascular anastomosis. During this procedure, the cut ends of two vessels are joined together such that blood can flow through the joined vessels. Vascular anastomosis is common in transplant surgery when the vessels of the donor organ are attached to existing vessels in the patient. Vascular anastomosis is also common when a severed extremity is reattached to a patient.

FIG. 1 shows a cuff 50 suitable for use in a vascular anastomosis procedure. Because the cuff 50 is cylindrical in shape, securely holding the cuff with a single pair of forceps (or a hemostat) 52 can be difficult. Because the single pair of forceps 52 only touches two points on the exterior of the cylindrical cuff 50, the cuff is free to rotate around those two points. In order to securely hold the cuff 50, a second pair of forceps (or a second hemostat) 54 must be used to grasp the cuff at a different angular orientation. By grasping the cuff with two pairs of forceps, the cuff can be securely held. Unfortunately, using two pairs of forceps is awkward and may require two hands, thus making any additional procedures very difficult.

FIG. 2 shows another type of anastomosis cuff 60, which has an extending tab 62. The extending tab 62 can be grasped by a single pair of forceps to hold the cuff relatively stable. However, because the walls of the cuff 60 are relatively thin, the extending tab 62 can flex relative to the main body of the cuff 60 when forces are applied to the cuff during an anastomosis procedure. The movement of the cuff 60 due to the flexing makes it difficult perform the anastomosis procedure. In addition, the location of the extending tab 62 makes the tab difficult to grasp, and may cause interference between the tab and surrounding body tissue.

FIGS. 3A–3D illustrate a typical anastomosis procedure using a prior art cuff 50. As shown in FIG. 3A, a cuff 50 is first fitted over a severed end 72 of a vessel 70. The cuff is then grasped with one or more pairs of forceps (not shown) and the end 72 of the vessel 70 is turned inside out around the end of the cuff 50, as shown in FIG. 3B. During this procedure, the cuff 50 must be held relatively steady to allow the end 72 of the vessel 70 to be turned inside out over the cuff 50. The enverted end 72 of the vessel 70 is then sutured to the cuff 50 with sutures 74 to immobilize the enverted end 72. The mating end of a second vessel 78 is then brought adjacent the enverted end 72 of the first vessel 70, as shown in FIG. 3C. Next, the end of the second vessel 78 is passed over the enverted end 72 of the first vessel 70, as shown in FIG. 3D. The second vessel 78 is then slid down over the enverted end 72 of the first vessel 70 and a circular suture 80 and knot 82 is placed around both of the vessels to hold the vessels securely together.

Because it is difficult to hold the cuff immobile during the anastomosis procedure, slippage of the cuff can occur during the procedure. This is particularly problematic if the exterior of the cuff is wet, or if the forceps are held at an imperfect angle. If two pairs of forceps are used to grasp the cuff at different angles, the vessel must be accessible enough for each pair of forceps to surround the cuff from different sides. If excessive pressure is applied to a cuff in an attempt to firmly grasp the cuff, the cuff may collapse, potentially ruining the underlying portion of the vessel.

SUMMARY OF THE INVENTION

It is an object of the invention to provide a manipulator tool that is capable of firmly grasping different types of anastomosis cuffs during vascular anastomosis. A manipulator tool according to the present invention has a pair of mating gripping fingers. Each gripping finger has an indentation shaped so that when the pair of fingers are mated together, the semicircular indentations form an aperture between the fingers. The aperture has a diameter that is slightly less than the exterior diameter of an anastomosis cuff so that the cuff may be securely grasped between the fingers by the walls of the cylindrical aperture without danger of cuff collapse.

BRIEF DESCRIPTION OF THE DRAWINGS

Preferred embodiments of the present invention will be described with reference to the following drawing figures, wherein like features are identified with like reference numbers, and wherein.

DETAILED DESCRIPTION OF PREFERRED EMBODIMENTS

Although the specification, claims and abstract refer to vascular anastomosis, the invention is equally applicable to an anastomosis procedure that joins the ends of any type of biological duct. The use of the term vessel or vascular herein is intended to encompass not only blood vessels, but also other types of biological ducts such as a bile duct, thoracic duct or a pancreatic duct.

Figure 1:
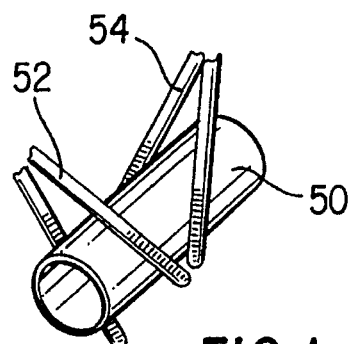
FIG. 1 is a perspective view of a prior art cuff grasped by two pairs of forceps.
Figure 2:
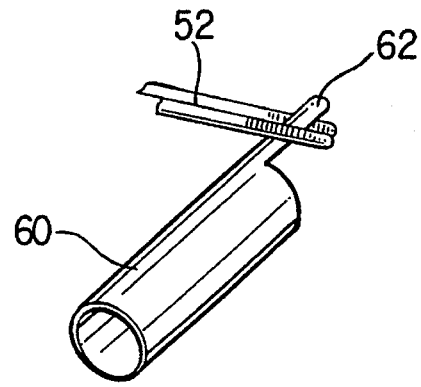
FIG. 2 is a perspective view of a prior art cuff grasped by a single pair of forceps.
Figure 3A:
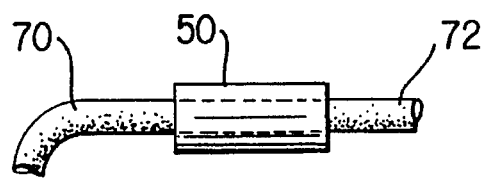
FIGS. 3A–3D illustrate a vascular anastomosis procedure.
Figure 3B:
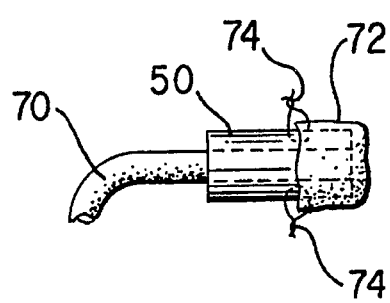
Figure 3C:
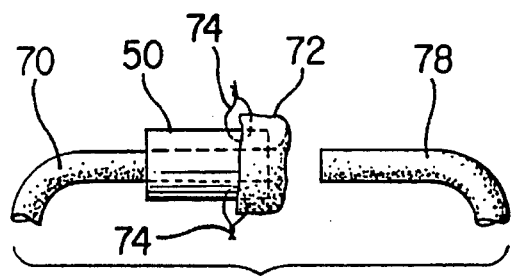
Figure 3D:
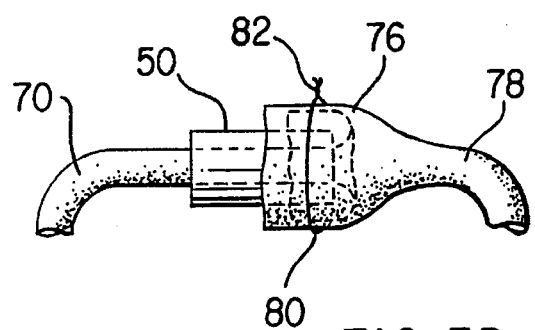
Figure 4:
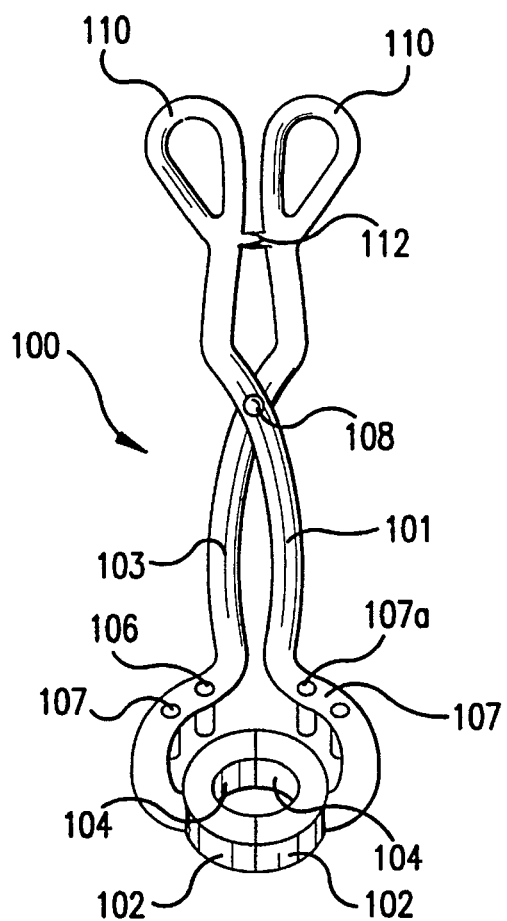
FIG. 4 is a front view of a manipulator tool embodying the present invention.

A manipulator tool embodying the present invention is shown in FIG. 4. The manipulator tool 100 includes two gripping arms 101, 103. The gripping arms 101, 103 end in gripping fingers 102, which mate together to grasp a cuff.

The gripping fingers 102 have semicircular indentations 104 that are shaped such that when the gripping fingers 102 mate together, the semicircular indentations 104 form a cylindrical aperture extending between the gripping fingers 102. The manipulator arms 101, 103 are rotationally mounted about a pin 108. Hand grips 110 are provided to allow a surgeon to grasp the tool and to open and close the tool.

Curved portions 107 of the gripping arms 101, 103 extend between main portions of the gripping arms 101, 103 and the gripping fingers 102. As shown in FIG. 4, the shape of the curved portions 107 creates an open area between the gripping arms 101, 103 that allows a surgeon to clearly view an underlying vessel.

Retractor pins 106 may be provided in the curved portions 107. The retractor pins 106 can be useful to retract internal organs and internal tissues away from the vessel which is the subject of the procedure.

A locking device 112 may be provided to keep the gripping arms 101, 103 closed at a certain position. The gripping arms 101, 103 and the locking device 112 may be designed such that when enough force has been applied to firmly hold a cuff between the gripping fingers 102, the locking device 112 may be engaged. The locking device would allow a cuff to be held between the gripping fingers 102 without the continual application of pressure to the gripping arms 101, 103.

Figure 5:
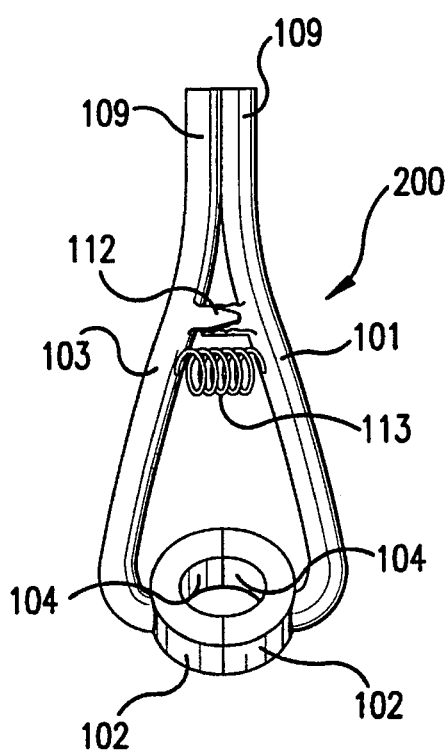
FIG. 5 is a front view of a manipulator tool embodying the present invention.

Another embodiment of the invention is shown in FIG. 5. In this embodiment, the ends 109 of the two gripping arms 101, 103 are joined together, and a spring 113 is attached between the gripping arms 101, 103 to bias the gripping arms apart. The gripping arms 101, 103 end in two mating gripping fingers 102. Each gripping finger 102 has a semicircular indentation 104. When the gripping fingers 102 are mated together, the semicircular indentations 104 form a cylindrical aperture between the gripping fingers 102. The user of the manipulator tool applies a force to the gripping arms 101, 103 to bring the gripping fingers 102 together to grasp a cuff between the walls of the cylindrical aperture formed by the semicircular indentations 104.

A locking device 112 may be provided to allow the manipulator tool to be closed at various positions. The gripping arms 101, 103 and the locking device 112 may be designed such that when enough force has been applied to firmly hold a cuff between the gripping fingers, the locking device 112 may be engaged. This allows a cuff to be held between the gripping fingers 102 without the continual application of pressure to the gripping arms 101, 103.

Figure 6:
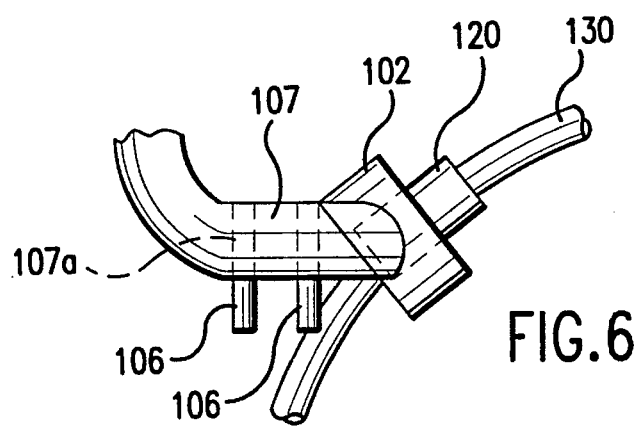
FIG. 6 is a side view illustrating the gripping arms and gripping fingers of a manipulator tool gripping a cuff surrounding a vessel.

A side view of the gripping arms 101, 103 and gripping fingers 102 of the manipulator device 100 is shown in FIG. 6. A cuff 120 is held between the gripping fingers 102 of the manipulator device. A blood vessel 130 passes through the cuff 120. FIG. 6 shows how the curved portions 107 are angled with respect to the main portions of the gripping arms 101, 103. FIG. 6 also shows how the gripping fingers may be angled with respect to the curved portions 107 such that the axis of the cylindrical aperture formed by the semicircular indentations 104 is angled with respect to the curved portions 107.

Figure 7:
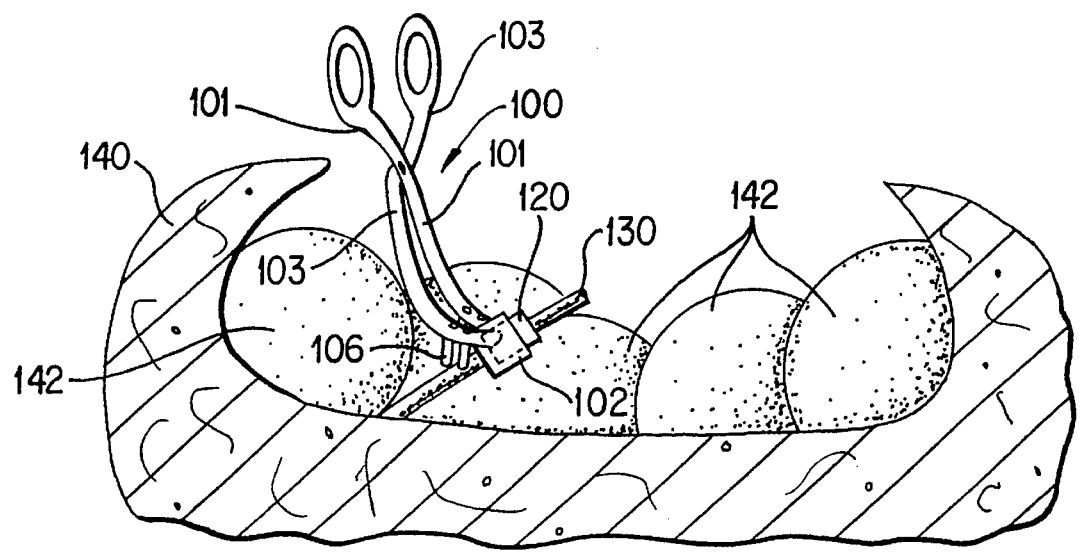
FIG. 7 illustrates a manipulator tool embodying the present invention gripping a cuff surrounding a vessel in a body cavity.

FIG. 7 shows how the curvature of the gripping arms 101, 103 and the orientation of the axis of the cylindrical aperture in the gripping fingers 102 helps to position the gripping fingers 102 of the manipulator 100 so that they can easily grip a cuff surrounding a vessel 130 in an interior body cavity of a patient 140. Internal organs 142 are located in the body cavity, and the vessel 130 extends between the internal organs 142. The gripping fingers 102 of the manipulator tool 100 must descend over these internal organs to reach the vessel 130. The retractor pins 106 aid in holding back the internal organs 142 so that the surgeon has a clear view down between the curved portions 107 of the gripping arms 101, 103 of the tool 100. The curved portions 107 of the gripping arms 101, 103, and the angular disposition of the semicircular indentations 104 of the gripping fingers 102 allow the tool to easily grip a cuff 120 surrounding a vessel 130 located deep inside a body cavity.

Figure 8:
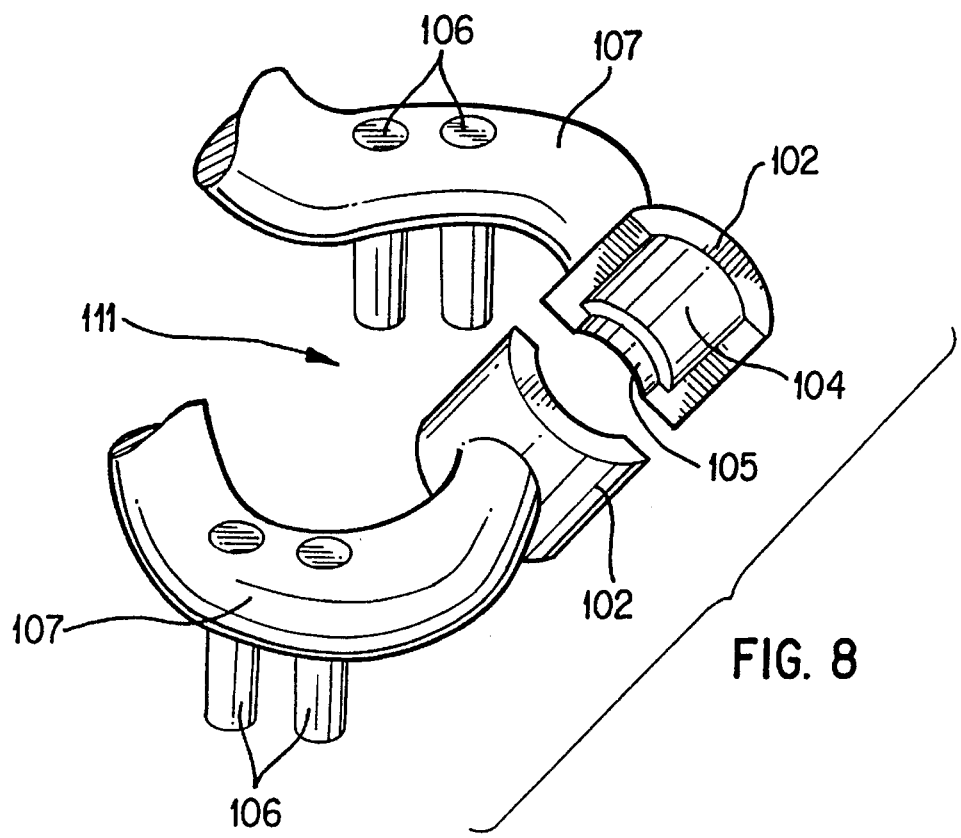
FIG. 8 is a perspective view of gripping arms and gripping fingers of a manipulator tool embodying the present invention.

The curved portions 107 and gripping fingers 102 of a manipulator tool embodying the invention are shown in FIG. 8. The curved portions 107 create a viewing area that allows a user to clearly see a blood vessel located below the manipulator tool. The gripping fingers 102 include a retaining lip 105 at the rear edge of the semicircular indentations 104. The retaining lip 105 abuts the rear edge of an anastomosis cuff when the cuff is grasped between the gripping fingers 102. The location of the retaining lips 105 ensures that the anastomosis cuff will not be forced out from between the gripping fingers 102 when axial forces are applied to the cuff during the anastomosis procedure.

Figure 9:
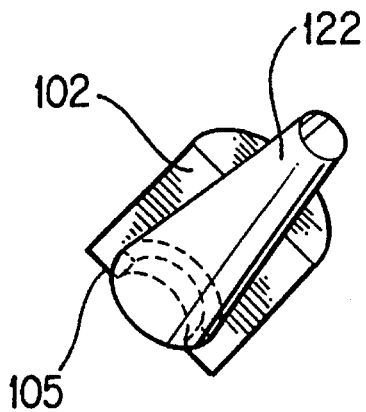
FIG. 9 is a perspective view of a conical shaped cuff gripped by one gripping finger of a manipulator tool embodying the present invention.
Figure 10:
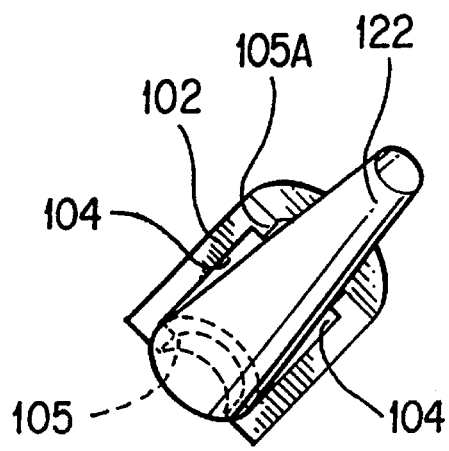
FIG. 10 is a perspective view of a conical shaped cuff gripped by one gripping finger of a manipulator tool embodying the present invention.

FIGS. 9 and 10 are perspective views showing conical-shaped anastomosis cuffs inside one gripping finger 102 of a manipulator tool. The remainder of the manipulator tool is not shown so that the details of how the cuff fits inside the gripping fingers 102 may be clearly illustrated. In FIG. 9, the walls of the semicircular indentations 104 of the gripping finger 102 are shaped to closely match the exterior walls of the conical shaped cuff 122. The shape of the walls ensures that the cuff 122 is firmly gripped by the gripping finger 102.

In FIG. 10, the gripping finger 102 has two retaining lips 105, 105a located at the front and rear edges, respectively, of the gripping finger 102. The remainder of the walls of the semicircular indentations 104 have a cylindrical shape similar to the gripping fingers shown in FIG. 11. This type of gripping finger 102 could also be used to firmly grasp a conical shaped cuff 122. The larger base of the cuff 122 is grasped by the larger diameter portion of the semicircular indentation 104, and the smaller diameter portion of the cuff 122 is grasped by the smaller diameter portion of the retaining lip 105a located on the front edge of the gripping finger 102. This type of gripping finger could also be used to firmly grasp a cylindrical shaped cuff, which could be trapped between both retaining lips 105, 105a.

Figure 11:
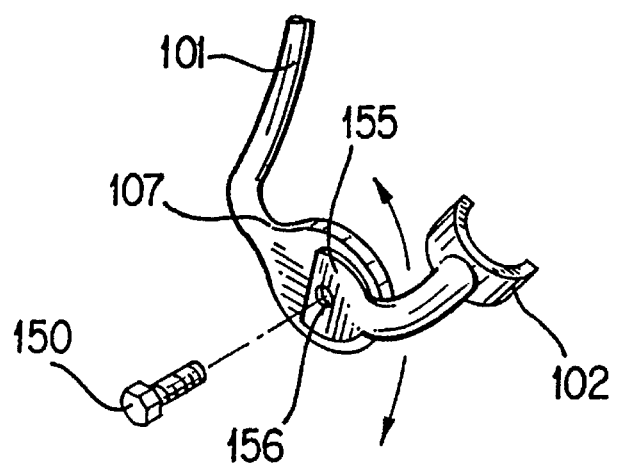
FIG. 11 is a perspective view of a gripping arm and an adjustable gripping finger of a manipulator tool embodying the present invention.

FIG. 11 shows a gripping arm 101 having a curved portion 107 and a removable, replacable, adjustable gripping finger 102. The gripping finger 102 is pivotally mounted on the curved portion 107 of the gripping arm 101. The gripping finger 102 is attached to the curved portion 107 by a screw 150 that passes through a rotatable plate 155, and is inserted into a threaded hole 156 in the curved portion 107. A gripping finger could also be attached to a gripping arm by any conventional means such as a pin, a snap ring, screws threads, nuts and bolts, leaf springs and pins, and other commonly known methods. The gripping finger 102 is capable of being fixed to the curved portion 107 at different rotational angular positions to facilitate gripping of an anastomosis cuff.

Various sized gripping fingers could be attached to a gripping arm of a manipulator tool embodying the present invention. The different sized gripping fingers would allow the tool to grasp different sized anastomosis cuffs. A gripping arm as shown in FIG. 11 would also allow gripping fingers designed for cylindrical shaped cuffs to be exchanged for gripping fingers designed for conical shaped cuffs. Having removable gripping fingers would also facilitate replacement of worn fingers without requiring replacement of the entire manipulator tool.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative and not limiting. Various changes may be made without departing from the spirit and scope of the invention as defined in the following claims.

What is claimed is:

1. A device for grasping a cuff during an anastomosis procedure, comprising:

first and second gripping arms, each of the first and second gripping arms having a gripping finger at a first end thereof, wherein the first and second gripping arms are movable with respect to one another to bring mating surfaces of the gripping fingers together, and wherein the mating surfaces of each of the gripping fingers have an indentation such that an aperture is formed between the gripping fingers for receiving a cuff when the gripping fingers are brought together, each of the first and second gripping arms further having a main body portion and a first curved portion located between the main body portion and the gripping finger, and wherein the first curved portions of the first and second gripping arms form a viewing aperture between the first and second gripping arms, a plane of the viewing aperture being oriented substantially perpendicular to a longitudinal axis of the first and second gripping arms, the viewing aperture permitting a user to view a surrounding area beneath the gripping fingers when the device is grasping the cuff.

2. The device of claim 1, wherein the indentation in each gripping finger is shaped such that a cylindrical aperture is formed between the gripping fingers when the gripping fingers are brought together.

3. The device of claim 1, wherein the indentation in each gripping finger is shaped such that a conical aperture is formed between the gripping fingers when the gripping fingers are brought together.

4. The device of claim 1, wherein each of the first and second gripping arms further comprise a second curved portion located between the main body portion and the first curved portion, the second curved portion causing a longitudinal axis of the first curved portion to be angled with respect to a longitudinal axis of the main body portion.

5. The device of claim 1, further comprising a locking mechanism connected to the first and second gripping arms for locking the first and second gripping arms in a particular position with respect to one another.

6. The device of claim 1, wherein the aperture formed between the indentations has a longitudinal axis oriented at an angle relative to a longitudinal axis of the first and second gripping arms.

7. The device of claim 1, wherein the aperture formed between the indentations has a longitudinal axis oriented at other than a right angle relative to a longitudinal axis of the first and second gripping arms.

8. The device of claim 1, wherein the gripping fingers are removably attached to the first and second gripping arms.

9. The device of claim 1, wherein the gripping fingers are adjustably attached to the first and second gripping arms.

10. The device of claim 9, wherein the aperture formed between the indentations has a longitudinal axis, wherein the first and second gripping arms have a longitudinal axis, and wherein the gripping fingers are adjustable to alter an angle between the longitudinal axis of the aperture and the longitudinal axis of the first and second gripping arms.

11. The device of claim 1, wherein the indentations are shaped such that ridges are formed at rear edges of the gripping fingers.

12. The device of claim 11, wherein the indentations are shaped such that an axial end of a cuff grasped between the gripping fingers abuts the ridges on the rear edges of the gripping fingers.

13. The device of claim 11, wherein the indentations are semicircular indentations, the semicircular indentations are shaped such that ridges are also formed at front edges of the gripping fingers.

14. The device of claim 1, wherein a spring is mounted between the first and second gripping arms, the spring biasing the gripping arms away from one another.

15. The device of claim 1, wherein the first gripping arm is pivotally mounted to the second gripping arm, pivotal movement between the first and second gripping arms bringing the mating surfaces of the gripping fingers together.

16. The device of claim 1, wherein second ends of the first and second gripping arms opposite the first ends are attached to one another.

17. The device of claim 16, wherein deformation of the first and second gripping arms causes the gripping fingers to be brought together.

18. The device according to claim 1, further comprising at least one retractor extending downwardly from each of the first curved portions, the at least one retractor being adapted to hold back an internal organ, wherein the at least one retractor retains the internal organ to prevent the organ from entering the viewing area.

19. A device for grasping a cuff during an anastomosis procedure, comprising:

first and second gripping arms, each of the first and second gripping arms having a gripping finger at a first end thereof, wherein the first and second gripping arms are movable with respect to one another to bring mating surfaces of the gripping fingers together, and wherein the mating surfaces of each of the gripping fingers have an indentation such that an aperture is formed between the gripping fingers when the gripping fingers are brought together, each of the first and second gripping arms having a main body portion and a first curved portion located between the main body portion and the gripping finger; and at least one retractor extending downwardly from each of the first curved portions, the at least one retractor being adapted to hold back an internal organ.

20. The device of claim 19, wherein the first curved portions of the first and second gripping arms form a viewing aperture between the first and second gripping arms, the viewing aperture permitting a user to view a surrounding area beneath the gripping fingers when the device is grasping the cuff, and the at least one retractor retains the internal organ to prevent the organ from entering the viewing area.

21. A device for grasping a cuff during an anastomosis procedure, comprising:

first and second gripping arms, each of the first and second gripping arms having a gripping finger at a first end thereof, wherein the first and second gripping arms are movable with respect to one another to bring mating surfaces of the gripping fingers together, and wherein the mating surfaces of each of the gripping fingers have an indentation such that an aperture is formed between the gripping fingers for receiving a cuff when the gripping fingers are brought together, each of the first and second gripping arms further having a main body portion and a first curved portion located between the main body portion and the gripping finger, and wherein the first curved portions of the first and second gripping arms form a viewing aperture between the first and second gripping arms, the viewing aperture permitting a user to view a surrounding area beneath the gripping fingers when the device is grasping the cuff; and at least one retractor extending downwardly from each of the first curved portions, the at least one retractor being adapted to hold back an internal organ, wherein the at least one retractor retains the internal organ to prevent the organ from entering the viewing area.

\* \* \* \* \*